Figure 1:
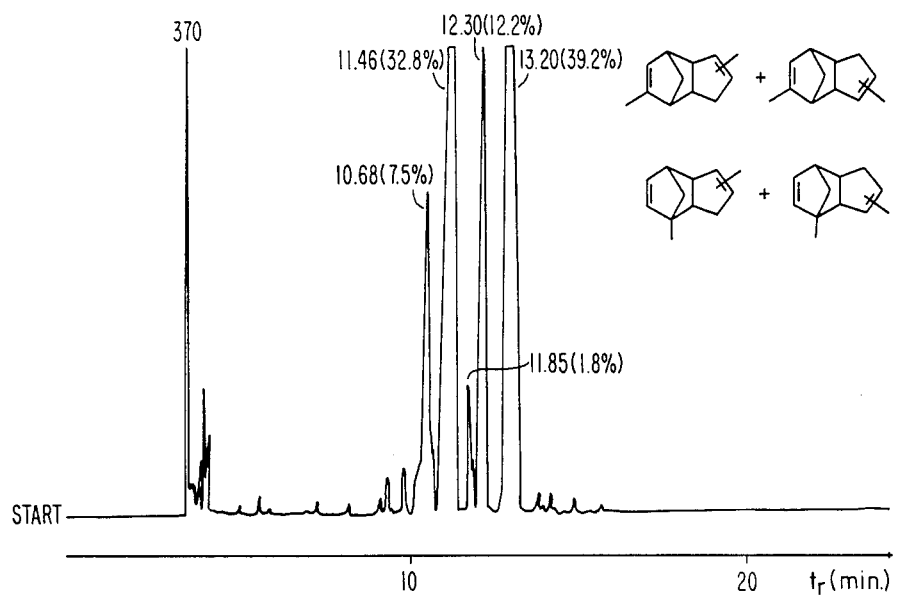

United States Patent [19]

Brunke et al.

[11] Patent Number: 4,683,083
[45] Date of Patent: Jul. 28, 1987

[54] MIXTURES OF TRICYCLO-DECANE-DERIVATIVES TOGETHER WITH THEIR PREPARATION AND USE AS PERFUMING-AND FLAVORING MATERIALS

[75] Inventors: Ernst-Joachim Brunke; Hartmut Struwe, both of Holzminden, Fed. Rep. of Germany

[73] Assignee: Dragoco Gerberding and Co. GmbH, Holzminden, Fed. Rep. of Germany

[21] Appl. No.: 691,567

[22] PCT Filed: May 10, 1984

[86] PCT No.: PCT/EP84/00141

§ 371 Date: Jan. 10, 1985

§ 102(e) Date: Jan. 10, 1985

[87] PCT Pub. No.: WO84/04520

PCT Pub. Date: Nov. 22, 1984

[30] Foreign Application Priority Data

May 13, 1983 [DE] Fed. Rep. of Germany ....... 3317476

[51] Int. Cl.[4] .............................. A61K 7/46; C11B 9/0
[52] U.S. Cl. .................. 252/522 R; 549/457; 558/260; 568/665; 568/817
[58] Field of Search .............. 252/522 R; 568/817, 568/665; 549/457; 558/260

[56] References Cited

U.S. PATENT DOCUMENTS

| | | | |
|---|---|---|---|
| 3,210,379 | 10/1965 | Porret | 568/665 |
| 3,280,152 | 10/1965 | Tinsley et al. | 568/817 |
| 4,123,394 | 10/1978 | Shorianetz et al. | 568/817 |
| 4,275,251 | 6/1978 | Sprecher et al. | 568/817 |
| 4,318,863 | 3/1982 | Sprecher et al. | 558/260 |
| 4,346,245 | 8/1982 | Sprecher et al. | 568/665 |
| 4,386,023 | 5/1983 | Sprecher et al. | 252/522 R |
| 4,410,740 | 10/1983 | Sprecher et al. | 568/817 |

FOREIGN PATENT DOCUMENTS

| | | | |
|---|---|---|---|
| 0039232 | 11/1981 | European Pat. Off. | 568/817 |
| 2654268 | 6/1977 | Fed. Rep. of Germany | 568/817 |
| 2642519 | 3/1978 | Fed. Rep. of Germany | 568/817 |
| 3208203 | 7/1983 | Fed. Rep. of Germany | 568/665 |
| 2334343 | 7/1977 | France | 568/817 |
| 0092750 | 8/1978 | Japan | 568/817 |
| 779241 | 7/1957 | United Kingdom | 568/817 |

OTHER PUBLICATIONS

Brown, "J. Amer. Chem. Soc.", vol. 85, (1963) pp. 1003–1005.
Klein et al., "Liebigs Annalen der Chemie" issue 11 Nov. 1973, p. 1797, etc.

Primary Examiner—Werren B. Lone
Attorney, Agent, or Firm—Hedman, Gibson, Costigan & Hoare

[57] ABSTRACT

The invention concerns
1. Mixtures of tricyclo[5.2.1.0$^{2,6}$]decane derivatives, having principal isomers corresponding to the general formula A, wherein $R^1$ and $R^2$ are hydrogen atoms or are a methyl group or a hydrogen atom, one of the substituents being a methyl group and the other a hydrogen atom, $R^3$ and $R^4$ are hydrogen atoms or are a methyl group or a hydrogen atom, one of the substituents being a methyl group and the other a hydrogen atom, Y is a tetrahydrofurane system at C-4/C-5 or a substituted oxymethyl group at C-5 and a hydrogen atom at C-4, $R^5$ is a hydrogen atom or a $C_1$–$C_6$-acyl-, $C_1$–$C_6$-alkyl-, $C_1$–$C_6$-alkenyl-, $C_1$–$C_4$-alkoxymethyl-, $C_1$–$C_2$alkoxycarbonyl-, formylmethyl-, or di-$C_1$–$C_4$-alkoxyethyl-group, and the broken lines indicate a C—C-single bond and a C—C-double bond or alternatively two C—C-single bonds.

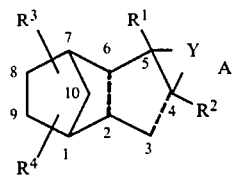

$R^1, R^2, R^3, R^4 = H$
$R^1, R^2 = H, CH_3 (1 \times CH_3)$
$R^3, R^4 = H, CH_3 (1 \times CH_3)$ (Abstract continued on next page)

-continued

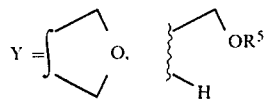

$R^5$ = $C_1$-$C_6$—acyl-, $C_1$-$C_6$—alkyl-, $C_1$-$C_6$—alkenyl-, $C_1$-$C_4$—alkoxymethyl-, $C_1$-$C_2$—alkoxycarbonyl, formylmethyl-, di-$C_1$-$C_4$—alkoxyethyl-group 2. Process for the preparation of these mixtures, wherein dimeric methylcyclopentadiene is selectively hydrogenated in the norbornane part and reacted with formaldehyde, paraformaldehyde or trioxane in the presence of a protonic acid or Lewis acid, optionally saponified or esters, ethers, acetates or oxoaldehydes prepared in known manner, and 3. the use of these mixtures as perfuming- and flavoring materials.

10 Claims, 13 Drawing Figures

MIXTURES OF TRICYCLO-DECANE-DERIVATIVES TOGETHER WITH THEIR PREPARATION AND USE AS PERFUMING-AND FLAVORING MATERIALS

The invention is concerned with mixtures of tricyclo[5.2.1.0$^{2,6}$]decane-derivatives and the use of these materials as perfumes or as aromas. These compounds are of the general formula A:

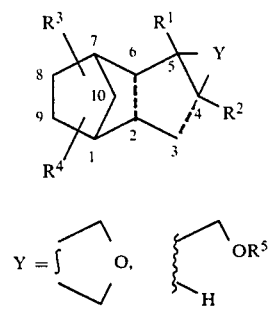

$R^1$ and $R^2$ are a methyl group or a hydrogen atom, one of the substituents being a methyl group and the other a hydrogen atom, $R^3$ and $R^4$ are a methyl group or a hydrogen atom, one of the substituents being a methyl group and the other a hydrogen atom, Y is a tetrahydrofurane system at C-4/C-5 or a substituted oxymethyl group at C-5 and a hydrogen atom at C-4, $R^5$ is a hydrogen atom or a C$_1$-C$_6$-acyl-, C$_1$-C$_6$-alkyl, C$_1$-C$_6$-alkenyl-, C$_1$-C$_4$-alkoxymethyl, C$_1$-C$_2$alkoxycarbonyl-, formylmethyl-, or di-C$_1$-C$_4$-alkoxyethyl group, and the broken lines indicate a C—C-single bond and a C—C-double bond or alternatively two C—C-single bonds.

The dimer of cyclopentadiene (1), dicyclopentadiene (2), is an important starting material for the production of perfume materials. The esters 3b-c (preparation: Zeilanov et al., Chem. Abstracts, 68, 49319d) obtained by the addition of carboxylic acids (e.g. acetic acid, propionic acid) are used in large amounts world-wide as perfume materials. The formate 3a is described in U.K. Pat. No. 815,232 (6.24.1959) and the dimethylacrylate 3d in U.S. Pat. No. 3,593,745 (8/10/1971). Further perfume materials from dicyclopentadiene were together described by Ohloff and Rodé-Sawal (in: H. Aebi, E. Baumgartner, H. P. Fiedler and G. Ohloff, "Nosmetika, Riechstoffe und Lebensmittelzusatzstoffe", G. Thieme Verlag, stutugart 1978, pp. 55-57).

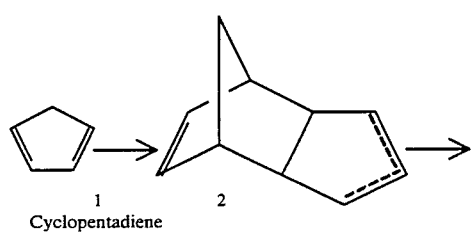

1 Cyclopentadiene    2

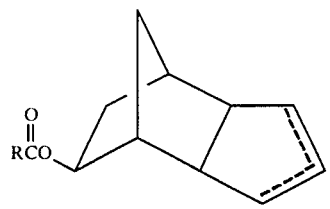

3a:R =H
3b:R =Me
3c:R =Et

3d:R =

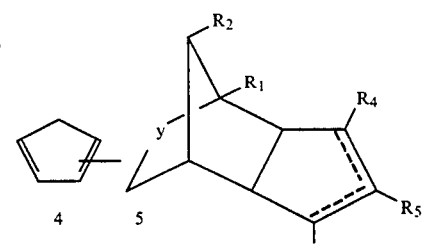

$R_1$, $R_2$ =H, CH$_3$/CH$_3$, H
$R_3$ =H, C$_1$-C$_3$—Acyl, C$_3$-/C$_4$-Alkyl-, C$_3$-/C$_4$—Alkenyl
$R_4$, $R_5$, $R_6$ =CH$_3$, H, H/H, CH$_3$, H/ H, H, CH$_3$ Little is known about the products of methylcyclopentadiene (4). In European Pat. appln. No. 0 039 232 were claimed as scents (perfume materials) dimethyltricyclodecane-derivatives of the general formula 5 obtained from the dimeric methylcyclopentadiene (4), the broken line representing an optional double bond. The methyl group in the norbornane part should alternatively be the R$_1$ or R$_2$ group and the methyl group in the cyclopentene part should alternatively be the R$_4$, R$_5$ or R$_6$ group. The respective non-substituted positions R$_1$, R$_2$, R$_{4-6}$ should be occupied by hydrogen. The molecular group Y should be a carbonyl-, hydroxyl-, acetate-, propionate-, or a C$_3$- or C$_4$- either group. The products consist of isomeric mixtures.

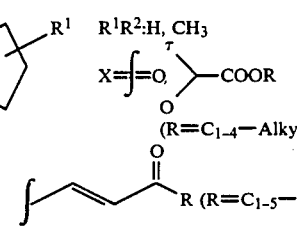

$R^1R^2$:H, CH$_3$

X=O, —COOR
(R=C$_{1-4}$—Alkyl)

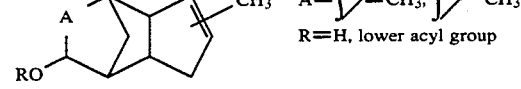

R (R=C$_{1-5}$—Alkyl)

A= =CH$_3$,  —CH$_3$
R=H, lower acyl group

German Pat. No. OLS 3 120 700 A1 (2/25/1982) describes tricyclodecane-derivatives of general formula 7 and their use as scents.

The preparation of the new compounds of general formula A started from dimeric methylcyclopentadiene.

Methylcyclopentadiene (preparation: review W. T. Ford, J.Org. Chem. 25, 3979 (1971)) exists as a mixture of three double-bonded isomers 4a, b, c. According to S. McLean and P. Haynes (Tetrahedron 21, 2313 (1965)) it exists in equilibrium as 44.5% of 1-methyl-isomer 4a, 54.5% of C-2-isomer 4b and only about 1% of c-5-isomer 4c.

Figure 2:
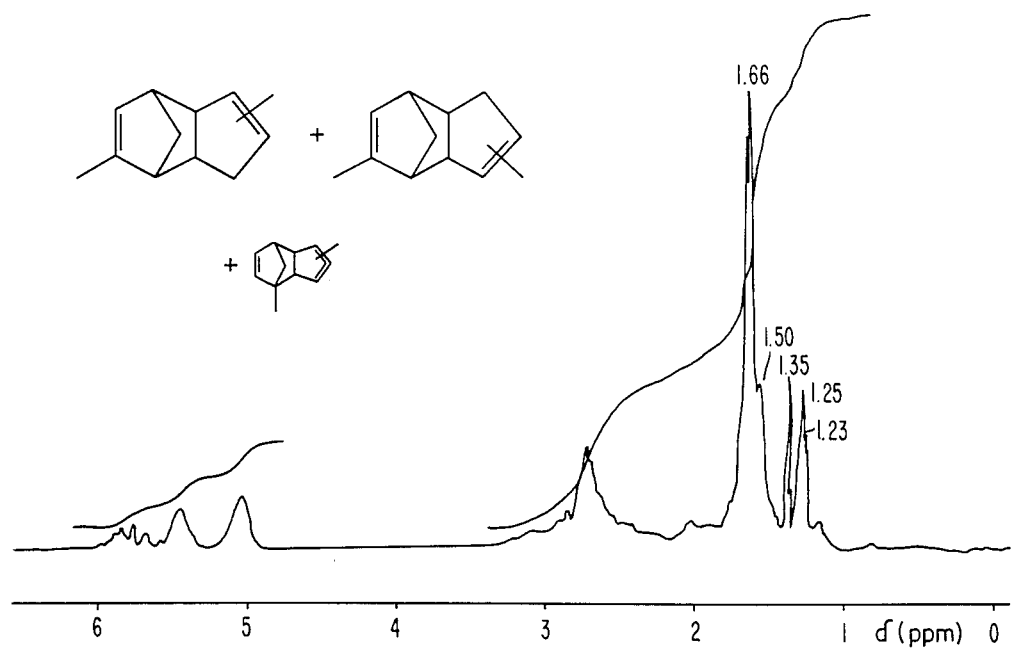

By the dimerization of anequilibrium mixture of methylcyclopentadiene a plurality of products can theoretically be prepared. By this hypothesis, products with angular methyl groups are sterically unfavorable and do not arise in significant amounts, and that product derived from 4c (<1%) can be ignored, so that the dimerised methylcyclopentadiene (gaschromatogram: FIG. 1) comprises the structural isomers 8a–h. The $^1$H-NMR-spectrum (FIG. 2) indicates signal groups in the range of olefinic protons (5–6 ppm), which correspond to their integral 2,2 protons. The signals at 1.25 and 1.50 ppm can by analogy with dicyclopentadiene (Sadtler-NMR-spectra collection No. 6494M) be classified as the protons of the $C_1$-bridge. Only the relatively low-intensity signals at 1.23 and 1.35 ppm can be classified as the bridging methyl group of 8a–d. These findings and the intensities of the olefinic signals point to the preponderant presence of isomers 8e–h (about 85%), while 8a–d exists as only about 15%.

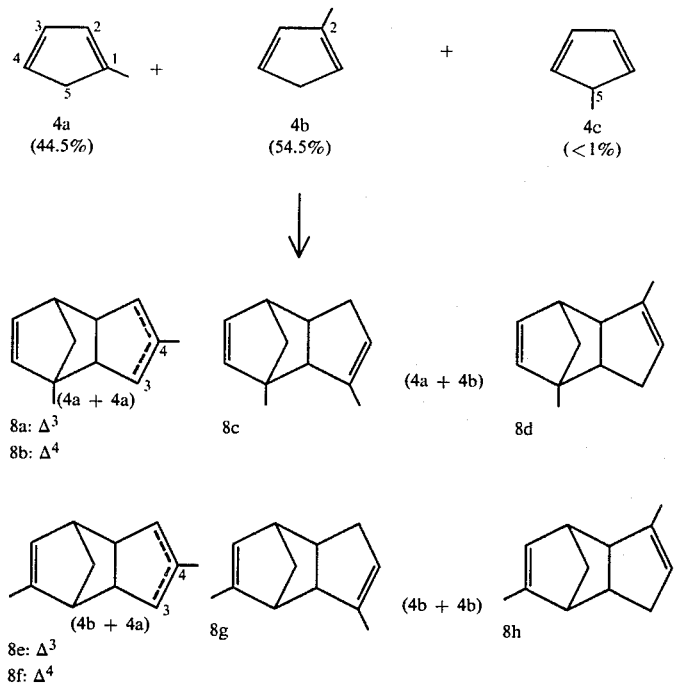

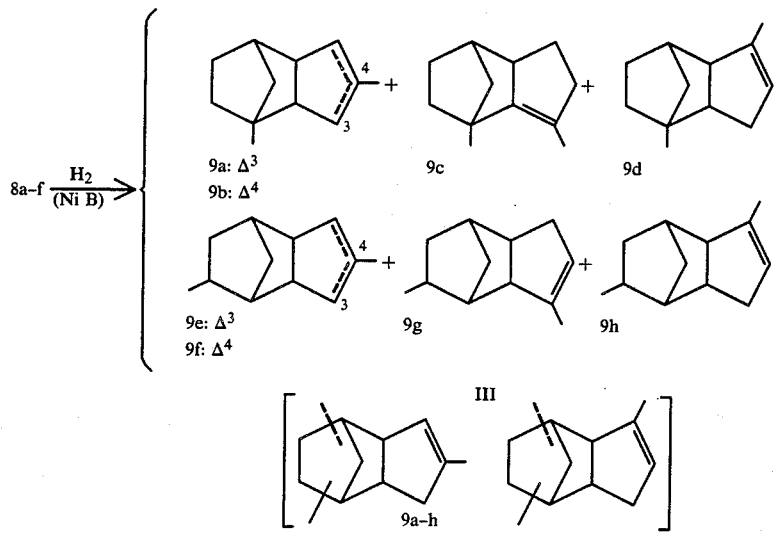

The selective hydrogenation of the norbornane part of the isomeric dimethylcyclopentadienes 8a–h is by a modification of a method of Ch. A. Brown for the selective hydrogenation of dicyclopentadiene (2) (Ch. A. Brown, Che. Commun. 1969, 952; H. C. Brown and Ch. A. Brown, J. Am. Chem. Soc., 85, 1004 (1963). Using nickel boride, prepared "in situ", followed by hydrogenation in methanol, ethanol or another polar, aprotic solvent at a temperature of 20°–80° C., preferably 40°–50° C., and a hydrogen pressure of 30–70 bar, preferably 50–60 bar. The mono-enes 9a–h thereby obtained exist according to GC (FIG. 3) as a mixture of three principal isomers (about 16, 24 and 37%) as well as further lower isomers, which like 8a–h can be treated as structural isomers but her also as stereo-isomers. All these isomers show a very similar mass-spectrometric fragmentation pattern, that can be explained by opening of the norbornane system in the formation of a methyl-cyclopentadienyl-radical (m/z 80) and a methylcyclopentane. In the $^1$H-NMR spectrum (FIG. 4) are the characteristic signals for olefinic protons at δ=5.1–5.3 ppm (1H) and that for olefinic methyl groups at 1.7 ppm for the cyclopentene system with tri-substituted double bond. Singlets at 1.25 and 1.15 ppm correlate with the main bridging methyl groups of the isomers 9a–c and two superimposed doublets at 1.05 ppm with the methyl groups of the norbornane part of the isomers 9d–f, that exist as principal isomers.

The new compounds of the general formula A can be approached from the mixture of olefines 9a–h by reaction with formaldehyde in the presence of acids. The mechanism of the reaction of olefines with formaldehyde ("Prins-reaction") under selective reaction conditions has been fully considered (review in: E. Klein, F. Thömel, A. Roth and H. Strwe, Liebigs Ann. Chem. 1973, 1797). The individual olefines of the mixture 9a–h react selectively with formaldehyde, that is the isomers 9a, b, e, f

Figure 5:
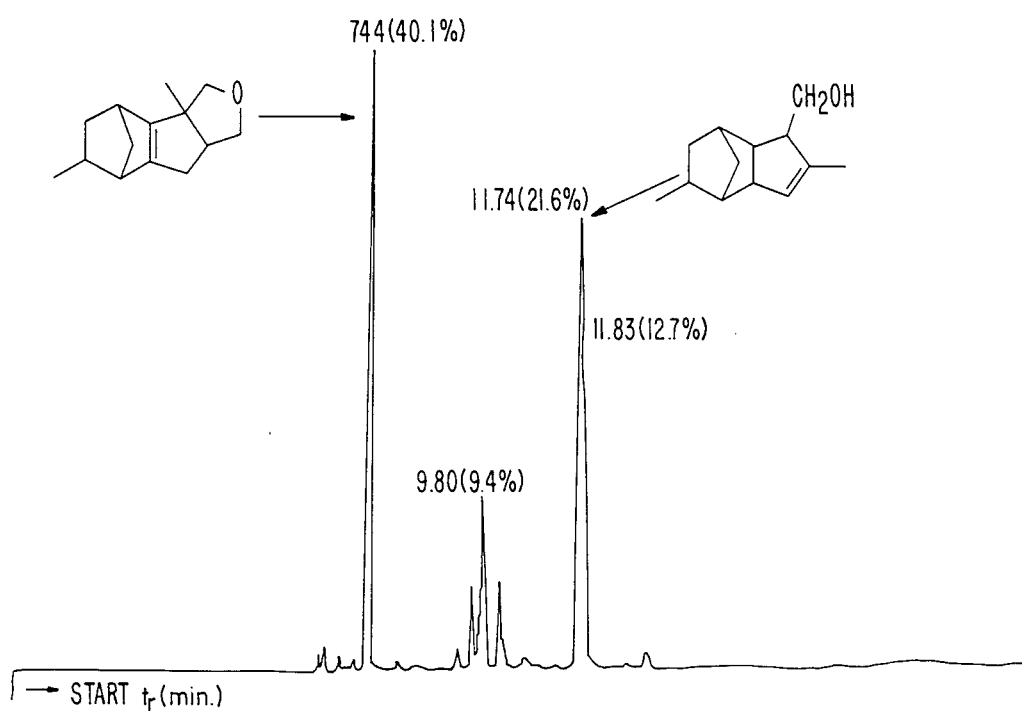
Figure 6:
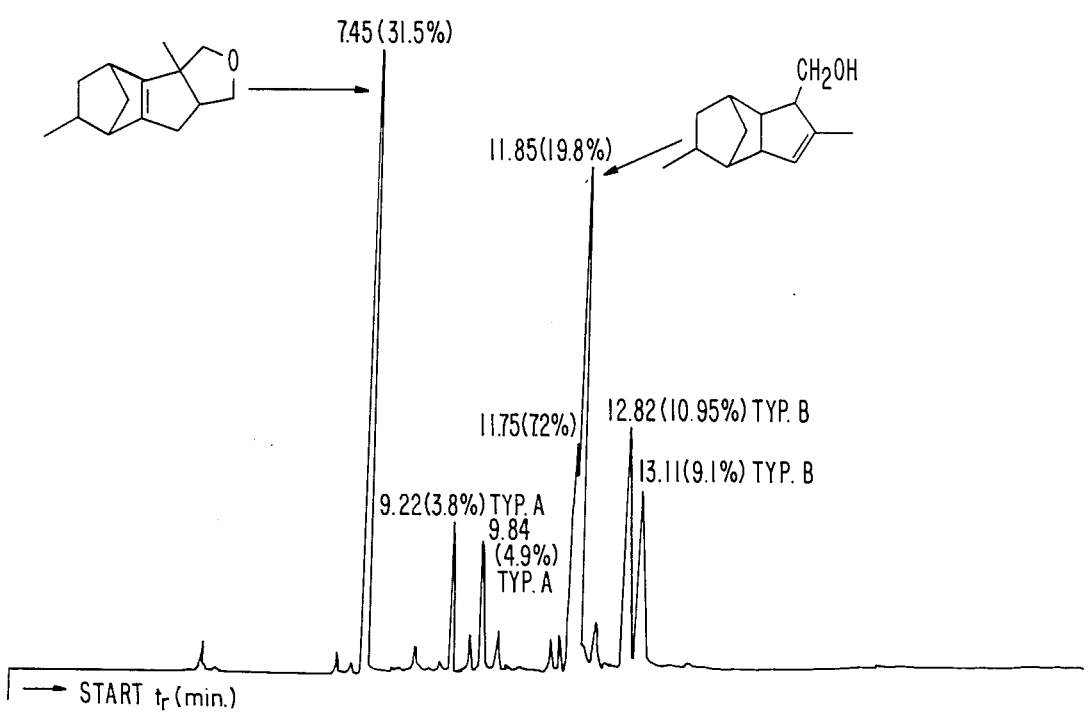

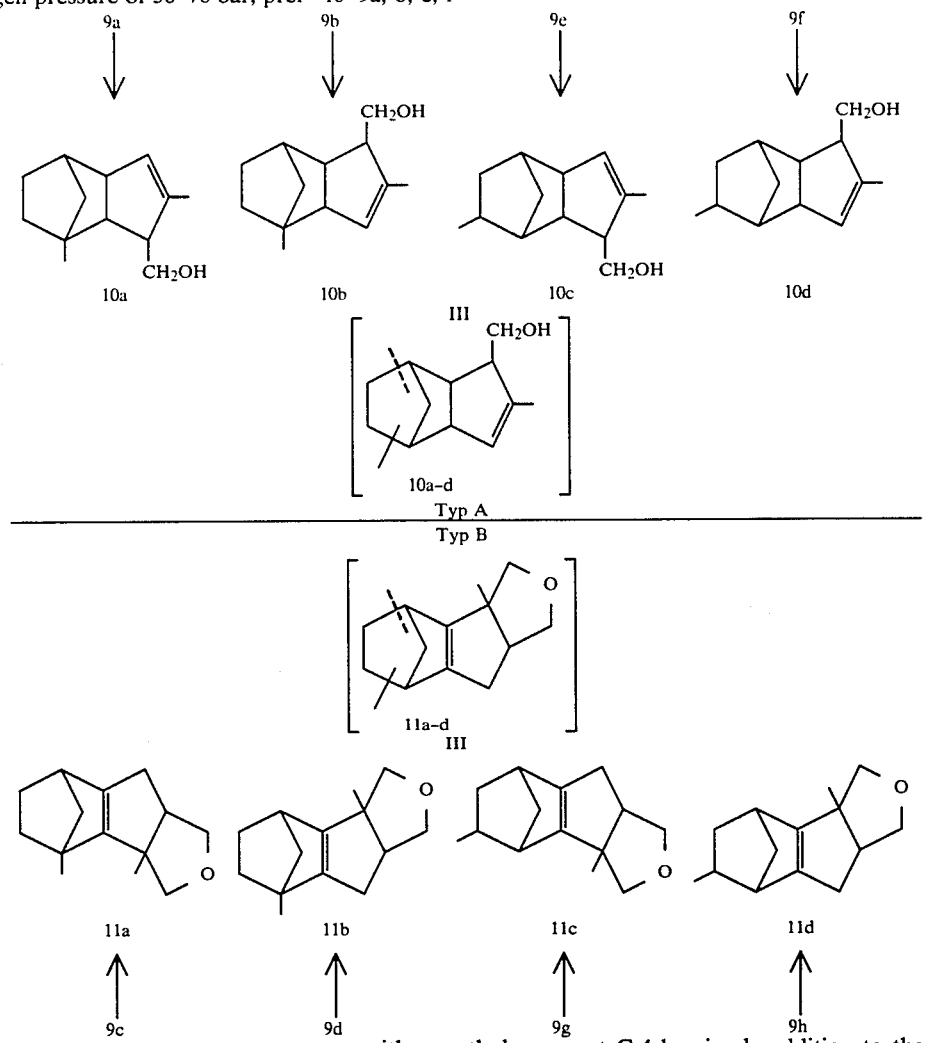

with a methyl group at C-4 by simple addition to the primary alcohols 10a–d (or the acetates 12a–d) of Type A and the isomers 9c, d, g, h with a methyl group at c-3 or C-5 by double addition to the tetracyclic ethers of Type B (11a–c). By use of p-toluene-sulfonic acid/acetic acid/acetic anhydride a mixture of the acetates 12a–d and 11a–d results and by use of formic acid (and alkaline working-up) a mixture of the alcohols 10a–d and 11a–d results. By selective reaction conditions the products of Types A and B were formed in variable proportions: by use of paraformaldehyde in acetic acid-/acetic anhydride with catalytic amounts of p-toluene-sulfonic acid (Examples 2/3; gaschromatogram of the saponified reaction mixtures: FIG. 5) the tetracyclic ether was produced in greater proportion than by use of paraformaldehyde in formic acid (Example 4; gas-chromatogram of the reaction mixture: FIG. 6). From the reaction mixtures (PTS, acetic acid, acetic anhydride) the principal isomers 11d and 12d were isolated by distillation.

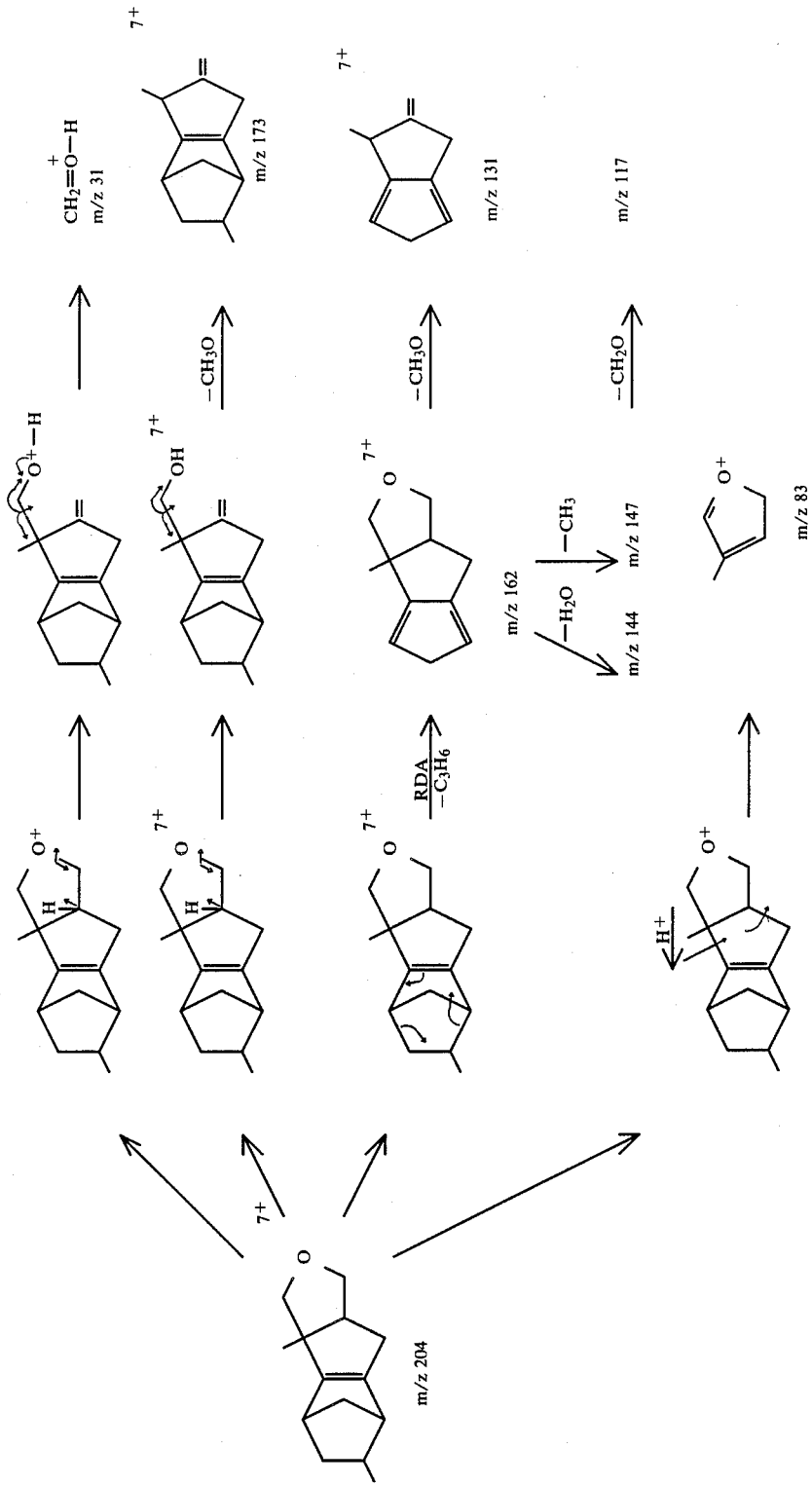

Figure 7:
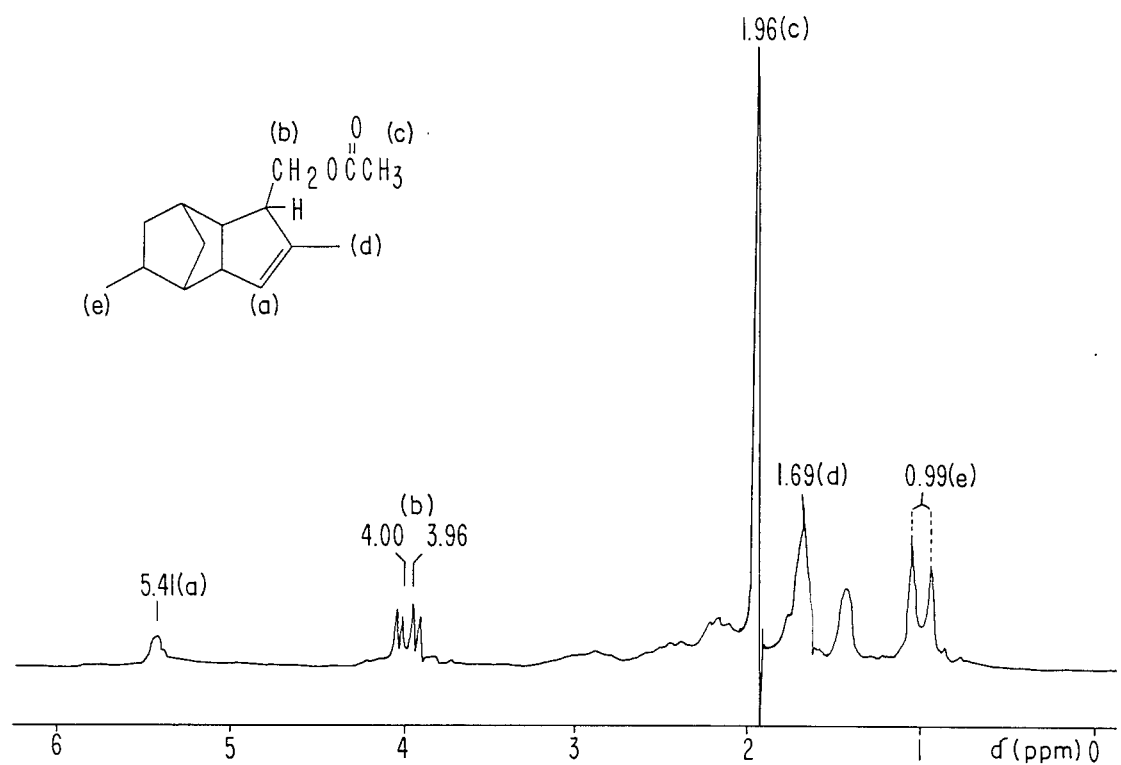
Figure 8:
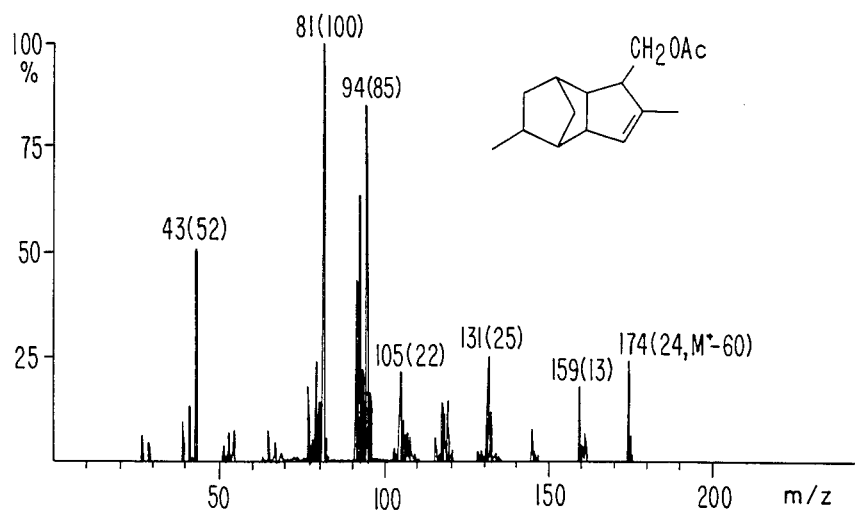

The constitution of 12d, the principal isomer of Type A, is shown from the $^1$H-NMR spectrum (FIG. 7) with a doublet at 0.99 (sec. methyl), a broad singlet at 1.69 and a multiplet at 5.41 ppm (olefinic system), and two doublets at 3.96 and 4.00 ppm (stereoisomeric acetoxymethyl-groups). The mass spectrometric fragmentation (FIG. 8) confirms the given structures.

The constitution of 11d, the principal isomer of Type B, was characterized in the H-NMR spectrum (FIG. 9) by a doublet at 0.84 ppm (sec. methyl), a singlet at 1.18 (allyl methyl), as well as multiplets at 3,4–4.0 ppm (tetrahydrofurane system) and in the $^{13}$C-NMR spectrum (FIG. 10) by singlet at 150 ppm (tetrasubstituted double bond). The essential mass spectrometric fragmentation of 11d may be interpretted without difficulty and stands in accord with the given structure.

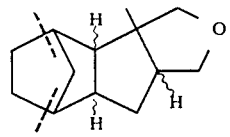

14a-d

By hydrogenation of the product-mixture of the Prins-reaction a selective saturation of the tri-substituted double-bond (compounds of Type A) can be obtained under normal conditions, so that mixtures of tricyclodecanes 13a-d with 11a-d result. Use of higher pressures (100–200 bar) and higher temperatures also give saturation of the tetra-substituted double bond and lead to mixtures of 13a-d with 14a-d.

| | | Smell Description | | |
|---|---|---|---|---|
| | | CH₂OR structure + 11a-d | | CH₂OR structure + 11a-d + 14a-d |
| R = H | 10a-d | fresh, woody, flowery | 15a-d | woody, fresh |
| R = acetyl | 12a-d | woody, spicy, sweet | 13a-d | woody, spicy, herby |
| R = propionyl | 16a-d | woody, spicy | 32a-d | woody, harsh |
| R = iso-butyryl | 17a-d | woody-sweet | 33a-d | woody |
| R = pivaloyl | 18a-d | mild-woody (condensed milk) | 34a-d | sweet, spicy-woody |
| R = tiglinyl | 19a-d | spicy, somewhat sweet | 34a-d | woody-sweet |
| R = crotonyl | 20a-d | woody-sweet (lovage) | 36a-d | woody, herby (celery) |
| R = methyl | 21a-d | woody, somewhat earthy | 37a-d | woody, somewhat like ambra |
| R = ethyl | 22a-d | woody, with ambra-note | 38a-d | woody, with ambra note |
| R = allyl | 23a-d | woody, fruity | 39a-d | fruity-woody |
| R = propyl | 24a-d | woody | 40a-d | woody |
| R = methoxycarbonyl (carboxylic acid ester) | 25a-d | woody, sweet-spicy | 41a-d | woody, somewhat medicine-like |
| R = ethoxycarbonyl | 26a-d | woody, sweet-spicy | 42a-d | woody, herby |
| R = formylmethyl | 27a-d | camphory, fresh-woody | 43a-d | camphory-woody |
| R = dimethoxyethyl | 28a-d | fresh, woody, fruity | 44a-d | fresh, woody |
| R = diethoxyethyl | 29a-d | fresh, woody, fruity | 45a-d | fresh, woody |
| R = ethoxymethyl | 30a-d | woody, spicy, sweet-harsh | 46a-d | woody, spicy |
| R = methoxymethyl | 31a-d | woody, spicy, sweet-harsh | 47a-d | woody, spicy |

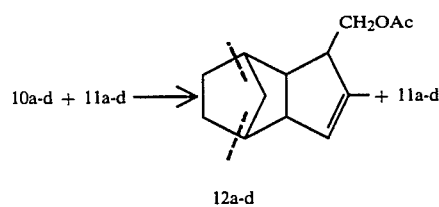

12a-d

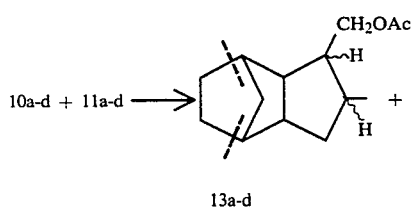

13a-d

From the saponified product mixture of the Prins-reaction, 10a-d+11a-d, as well as the product mixture of selective hydrogenation 13a-d+11a-d or of the complete hydrogenation 13a-d+14a-d, the corresponding derivative of the alcohol-component (Type A) can be prepared in manner, such as esters, ethers, acetates, carboxylic acid esters and oxoacetaldehyde, that are then respectively presented as mixtures with the tetracyclic eters (Type B).

The mixture of new compounds of general formula A possess woody, fresh or spicy odor notes, making them useful in perfumes and in formulating perfumed compositions.

The following examples illustrate the invention, without limiting the claims.

EXAMPLE 1

Figure 3:
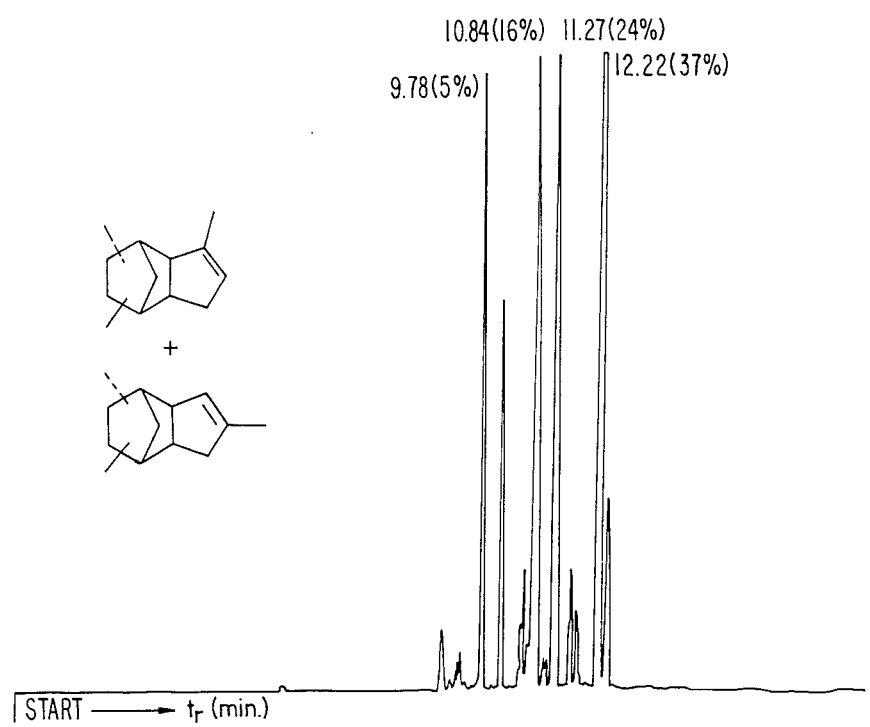
Figure 4:
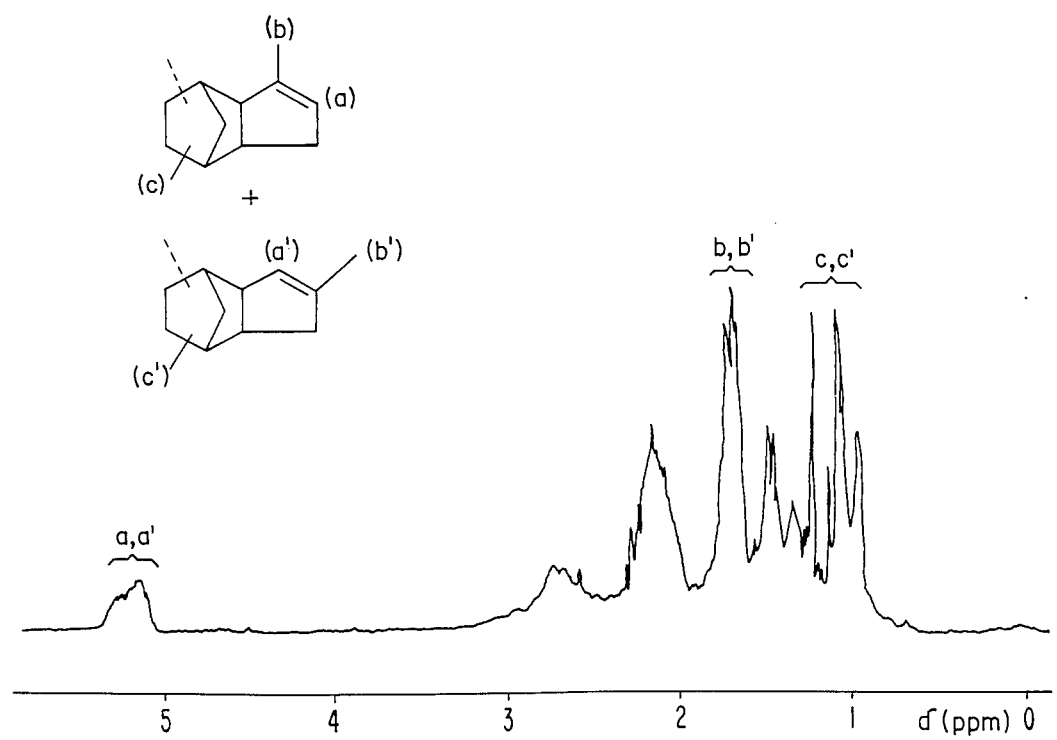

Preparation of the dimethyl-tricyclo[5.2.1.0$^{2,6}$]decenes 9a-h 150 ml of an ethanolic 1 m NaBH₄-solution were added dropwise with stirring into a mixture of 139.5 g (0.56 mol) Ni(Ac)₂.4H₂O and 1.9 l ethanol under a nitrogen atmosphere (15 min.) The nickel boride falls from this as a fine-grain, black deposit. After the addition of 1.44 kg (9 mol) of dimeric methylcyclopentadiene the nitrogen atmosphere is exhausted. Hydrogenation follows within 16 hours in a hydrogen atmosphere at 50-60 bar and a temperature of 40°-50° C. After, filtration, separation and distillation 2.57 kg (88%) 9a-h remained as a colorless oil; bp (2.6 bar)=76°-82° C.; density: $d_4{\cdot}^{20°}=0.9417$; refraction $n_D^{20°}=1.4989$. GC: FIG. 3 $^1$H-NMR: FIG. 4 $C_{12}H_{18}$ (162.4).

EXAMPLE 2

Brins-reaction on 9a-h (with p-toluenesulfonic acid)

A solution of 1296 g (8 mol) 9a-h in 1240 g acetic acid (anhydrous) was added with stirring to 74.4 g p-toluenesulfonic acid and 457.6 (15.3 mol) paraformaldehyde, and slowly heated to 90° C. After 1 hour stirring at 90° C. 137.6 g acetic anhydride was run in over 30 minutes. The reaction mixture was stirred 6 hours at 90° C. After cooling 1.8 l water was added and it was extracted with petroleum ether. The worked-up organic phase was separated and distilled over a 20 cm Vigreux-column. 1250 g end-product was yielded; bp (1.0 mbar)=75°-165° C. By fractionation of the end-product 875 g (47%) 12a-d+11a-d were obtained as a colorless oil; $n_D^{20°}=1.5001$, $d_4{\cdot}^{20°}=1.0254$.

By distillation with a rotary column main products 12d and 11d were isolated from the product mixture 12a-d+11a-d.

5-acetoxy-4,9-dimethyl-tricyclo[5.2.1.0$^{2,6}$]decene-3 (12d)

colorless oil; $n_D^{20°}=1.4932$, $d_4{\cdot}^{20°}=1.0265$. $^1$H-NMR (60 MHz, CCl$_4$): $\delta=0.99$, d, J=6.5 Hz (9-CH$_3$), 1.65, br.s (4—CH$_3$), 1.96, s (—CH$_2$—O—CO—CH$_3$), 1740 cm$^{-1}$ (ester). MS: m/z(%)=174(24, M+-60), 159(18), 132(12), 131 (25), 119(15), 118(10), 117(15), 105(22), 95(85), 93(21), 92(64), 91(43), 81(100), 80(14), 79(24), 77(18), 43(52), 41(13). $C_{15}H_{22}O_2$ (234.34).

Figure 9:
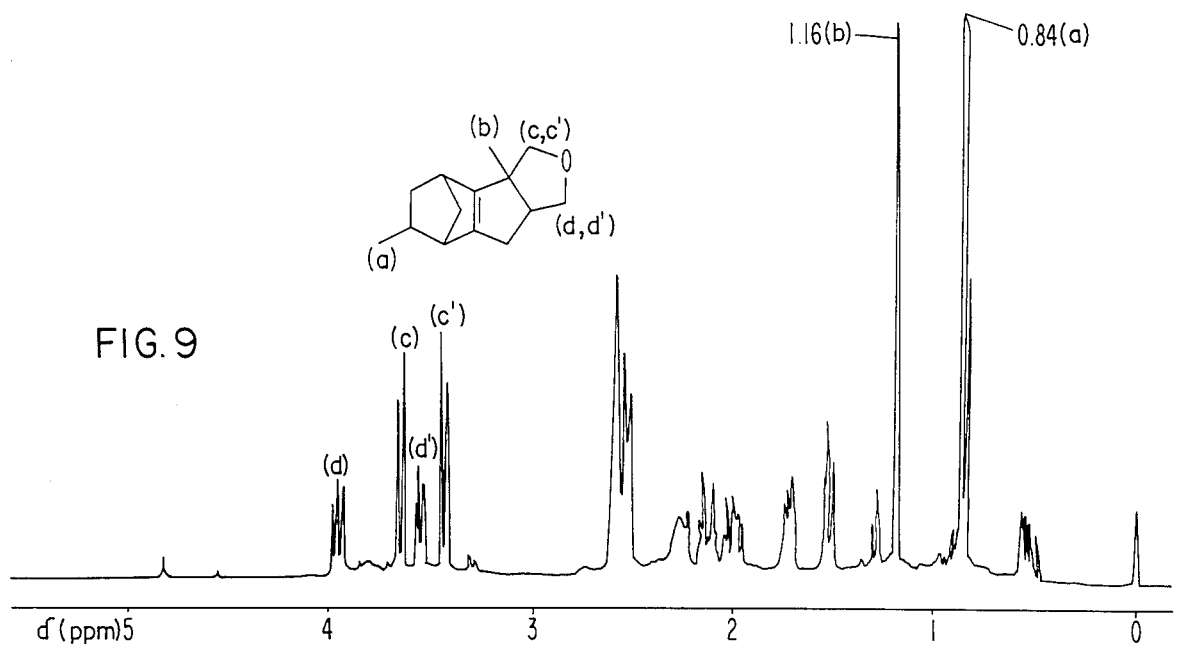
Figure 10:
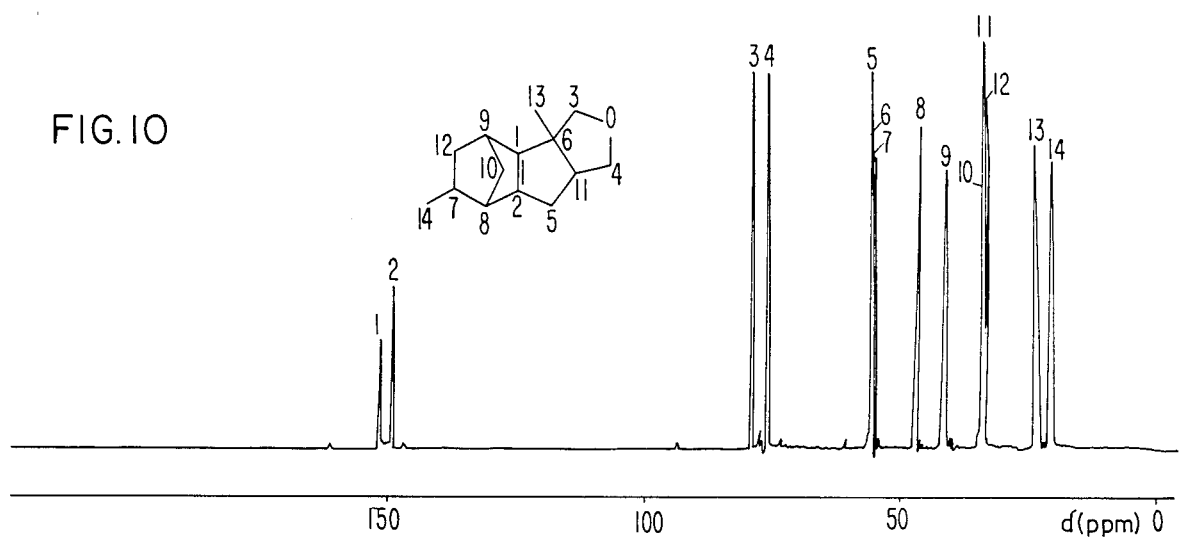
Figure 11:
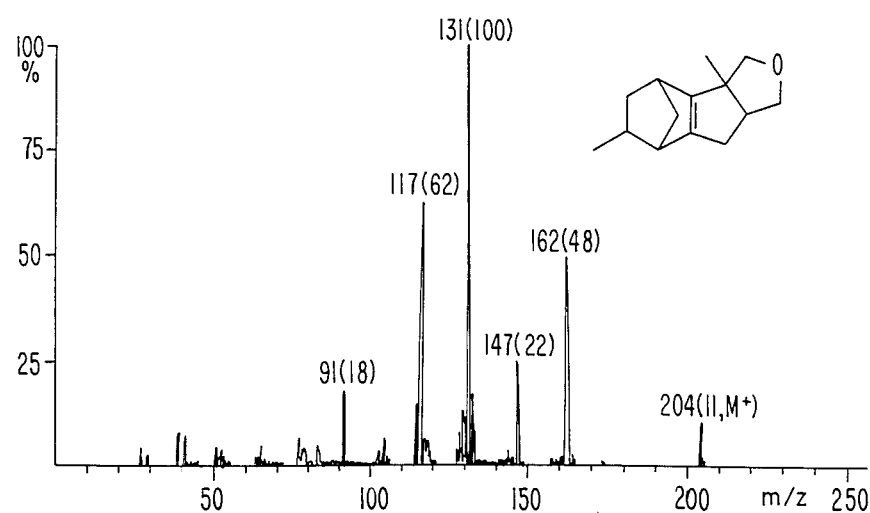
Figure 12:
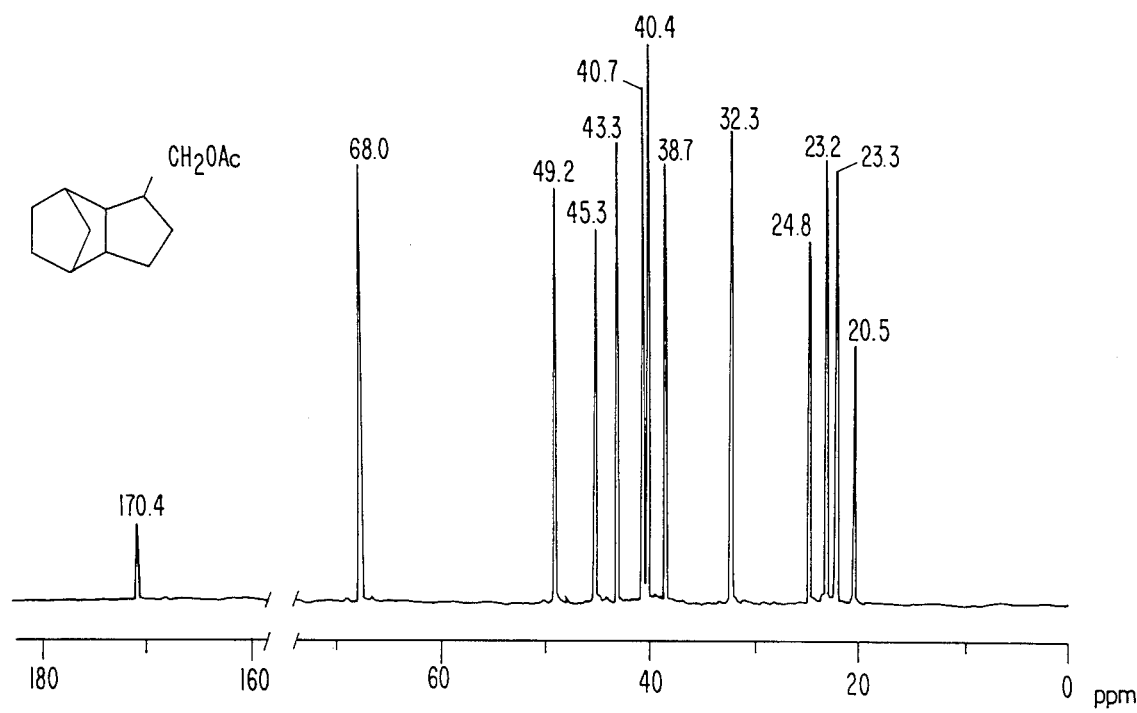
Figure 13:
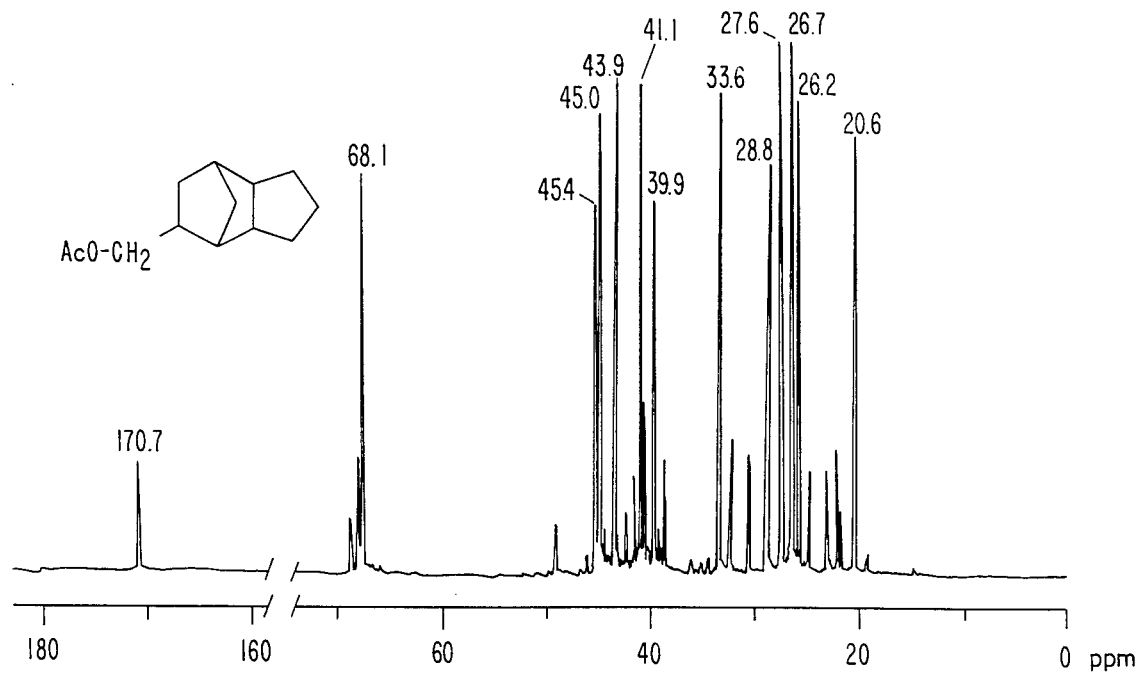

4,5tetrahydrofurano-5,9-dimethyltricyclo[5.2.1.0$^{2,6}$]-decene-2 (11d)

colorless oil; $n_D^{20°}=1.5063$, $d_4{\cdot}^{20°}=1.0232$. $^1$H-NMR(60 MHz, CCl$_4$; FIG. 9: 0.84, d, J=6.5 Hz (9—CH$_3$), 1.18, s (5—CH$_3$), 3.4-4.0 ppm, m(—CH$_2$—O—CH$_2$). $^{13}$C-NMR (FIG. 10): 20.71(q), 23.86(q), 33.65(t), 34.22(d), 34.31(t), 41.59(d), 46.26(d), 55.04(d), 55.52(s), 55.61(t), 75.95(t), 79.01(t), 149.20(s), 151.50 ppm(s). IR: 1070, 1065, 1040, 1005 cm$^{-1}$ (ether). NS: m/z (%)=204 (11, M+), 162(48), 147(@@), 132(15), 131(100), 130(12), 129(13), 117(62), 115(15), 91(18), 39(9). $C_{14}H_{20}O$ (204.31).

EXAMPLE 3

Saponification of 12a-d+11a-d

A solution of 117 g 12a-d+11a-d (mixture from Example 2) and 26 g NaOH in 350 ml methanol and 9 ml water were heated 1.5 hours to boiling. After the solvents were distilled off, 150 ml water were added. It was extracted with benzine, worked up, the end-product distilled over a 20 cm Vigreux-column and yielded 90.2 g (94%) 10a-d+11a-d; bp (1.3 mbar)=98° C., $n_D^{20°}=1.5117$, $d_4{\cdot}^{20°}=1.0233$. Gaschromatogram FIG. 5. The isomer 10d was isolated by fractional distillation over a rotary column.

5-hydroxymethyl-4,9-dimethyl-tricyclo[5.2.1.0$^{2,6}$]decene-3 (10d)

colorless oil; $^1$H-NMR(CCl$_4$): 0.97, d, J=7 Hz (9—CH$_3$), 172, br.s(4—CH$_3$), 3.5, s(—CH$_2$—OH), 5.33 ppm(3-H). IR: 3350 cm$^{-1}$ (OH). MS: m/z(%)=192(15, M+), 177(2), 174(5), 161($@), 131(6), 119(11), 110(17), 105(32), 95(30), 91(39), 81(100). $C_{13}H_{20}O$ (192.30).

EXAMPLE 4

Prins-reaction on 9a-h (in formic acid)

22.5 g (0.75 mol) paraformaldehyde was suspended in 125 ml anhydrous formic acid and stirred at boiling temperature until a clear solution was obtained (about 5 min). 81 g (0.5 mol) olefine mixture 9a-h was run in at about 30° C. (mildly exothermic reaction). The reaction mixture was stirred 20 hours at 38° C., 300 ml water were added after cooling and it was extracted with benzine. The combined organic phases were stirred 30 minutes with caustic soda solution(20%), then washed neutral and separated. Distillation over a 20 cm Vigreux-column gave 57.0 g (60%) 10a-d+11a-d as a colorless oil; bp (2 mbar) 85°-115° C., $n_D^{20°}=1.5130$, $d_4{\cdot}^{20°}=1.0277$. Gaschromatogram: FIG. 6.

EXAMPLE 5

Hydrogenation of 11a-d+12a-d (a) selective hydrogenation of 12a-d 500 mg of platinum-(IV)-oxide was added to a solution of 152 g 11a-d+12a-d (product of Example 2) in 400 ml anhydrous acetic acid and shaken in a hydrogen atmosphere under normal conditions until the take-up of hydrogen was complete. After removal of the hydrogen, it was filtered, separated and distilled over a 20 cm Vigreux-column. It yielded 129 g (85%) 11a-d+13a-d as a colorless oil; bp (1 mbar)=96°-115° C., $n_D^{20°}=1.4953$, $d_4{\cdot}^{20°}=1.9186$. GC/MS: $t_r$(%)=30.3(34, 11d), 34.07(5, M=206), 34.7(3, M=206), 34.9(6, M=236), 35.2(3, M=204), 36.5(12, M=236), 36.8(22, M=236), 37.1 (2.5, M=236).

(b) complete hydrogenation 3 g Raney-nickel was added to a solution of 152 g 11a-d+12a-d (product mixture from Example 2) in 400 ml anhydrous acetic acid and stirred at 100° C. in an 150 ml hydrogen atmosphere until the take up of hydrogen was complete. After removal of the hydrogen, it was filtered, separated and distilled over a 20 cm Vigreux-column. It yielded 121 g (82%) 13a-d+14a-d as a colorless oil.

5-acetoxymethyl-4,9-dimethyltricyclo[5.2.1.0$^{2,6}$]decane (13d)

MS (Type A): m/z(%)=176(10, M+—60), 161(18), 147(16), 134(100), 133(83), 121(29), 119(34), 107(29), 106(27), 105(34), 93(71), 79(68). $C_{15}H_{24}O_2$ (236.35).

4,5-tetrahydrofuran-5,9-dimethyltricyclo[5.2.1.0$^{2,6}$]decane (14d)

MS (Type B): m/z(%)=206(1, M+), 176(16), 161(14), 147(20), 134(15), 121(12), 120(12), 107(21)93(34), 81(84), 80(100). $C_{14}H_{22}O$ (206.32).

EXAMPLE 6

Saponification of 13a-d+11a-d

A mixture of 15a-d +11a-d was obtained in a manner analogous to Example 3; $n_D^{20°}=1.5061$, $d_4{\cdot}^{20°}=1.0151$.

5-hydroxymethyl-4,9-dimethyltricyclo[5.2.1.0$^{2,6}$]decane (15d)

MS: m/z(%)=194(6, M+), 176(12), 163(64), 147(6), 121(32), 107(41), 105(18), 94(24), 93(32), 81(100), 80(84), 79(46), 67(31), 55(27). $C_{13}H_{22}O$ (194.30).

EXAMPLE 7

Esterification of 10a-d+11a-d, 13a-d+11a-d, 13a-d+14a-d

A mixture of 77 g (0.4 mol, with reference to 10a-d or 15a-d) of the product mixture according to Example 3 (or according to Example 6) and 0.8 mol of the respective acid anhydrides was added by portions with stirring to 19.5 g sodium carbonate at 60°–80° C. After 6 hours stirring at 80°–85° C. and cooling, 200 ml water was slowly added, extracted with benzine, worked up and distilled over a 20 cm Vigreux-column. Each ester was obtained in a yield of 75–85%.

| | | $n_D^{20°}$ | $d_4^{20°}$ |
|---|---|---|---|
| acetate | 12a-d (+11a-d) | 1.5001 | 1.0254 |
| propionate | 16a-d (+11a-d) | 1.4981 | 1.0178 |
| isobutyrate | 17a-d (+11a-d) | 1.4960 | 1.0113 |
| acetate | 13a-d (+11a-d) | 1.4953 | 1.0186 |
| crotonate | 20a-d (+11a-d) | 1.5021 | 1.0233 |

EXAMPLE 8

Preparation of the methyl- or ethyl-ethers 21a-d+11a-d, 22a-d+11a-d

To a solution of 77 g (0.4 mol, with reference to 10a-d, or 15a-d) of the product mixture according to Example 3 (or Example 5) and 4 g "Aliquat 336" in 240 ml benzine 82 g caustic soda solution (50%) were added dropwise over 1.5 hours at 20°–50° C. After 1 hour stirring at 45° C. 103 g (87 ml, 0.67 mol) diethyl sulfate or 84 g (63 ml, 0.7 mol) dimethyl sulfate were run in and stirred about 20 hours at 45° C. Extraction with benzine, working up and distillation over a 35 cm Vigreux-column gave 66 g (60%) 22a-d+11a-d, bp (1.3 mbar)=93°–96° C. $n_D^{20°}=1.4984$, $d_4^{20°}=0.9916$ or 61.5 g (58%) 21a-d+11a-d, bp (1.8 mbar)=88°–91° C. $n_D^{20°}=1.5019$, $d_4^{20°}=1.0020$.

5-ethoxy-4,9-dimethyltricyclo[5.2.1.0$^{2,6}$]decene-3 (22d)

MS: m/z(%)=220(10, M+), 161(40), 119(20), 118(32), 105(25), 95(11), 94(14), 93(21), 92(10), 91(16), 81(100), 79(21), 77(14), 55(14). $C_{15}H_{24}O$ (220.35).

5-methoxy-4,9-dimethyltricyclo[5.2.1.0$^{2,6}$]decene (21d)

MS: m/z(%)-206(17, M+), 161(74), 159(18), 123(17), 119(27), 118(28), 109(16), 105(40), 93(30), 91(32), 81(100), 79(20), 77(19), 45(36). $C_{14}H_{22}O$ (206.33).

EXAMPLE 9

Preparation of the allyl ethers 23a-d+11a-d

To a solution of 43 g (about 0.23 mol) of the product mixture of Example 3, or Example 5 in 67 ml of toluene were added 13.5 g powdered sodium hydroxide and 3.4 g Aliquat 336. 21 g allyl chloride were added dropwise at about 40° C. with stirring. After 12 hours stirring at 40°–45° C. 100 ml water were added, and it was extracted with benzine and worked up. Distillation over a 20 cm Vigreux-column gave about 55 g of product mixture 23a-d+11a-d.

bp (1.5 mbar)=88°–90° C. $n_D^{20°}=1.5031$, $d_4^{20°}=0.9981$. 23d: $C_{16}H_{24}O$ (232.27, determined by MS).

EXAMPLE 10

Preparation of the pivalinates 18a-d+11a-d 84.3 g pivalin acid chloride were added dropwise (about 30 min) to a solution of 67.2 g (about 0.35 mol) of the product mixture of Example 3 in 250 ml dried pyridine. After 2 hours stirring at about 55° C. it was worked up. Distillation over a 20 cm Vigreux-column gave ester mixture 18a-d+11a-d, bp (1.5 mbar)=118°–122° C., $n_D^{20°}=1.4942$, $d_4^{20°}=1.0026$.

18d: $C_{18}H_{28}O_2$ (276.42, determined by MS).

EXAMPLE 11

Preparation of carboxylic acid esters

A solution of 67.5 g of the product mixture of Example 3 in 36 g pyridine and 276 ml dried toluene was added dropwise at about 0° C. to 49.5 g chloroformic acid ethylester while stirring. After 10 hours stirring 300 ml water were added. Working up and distillation gave 71 g of product mixture 16a-d+11a-d; $n_D^{20°}=1.4963$, $d_4^{20°}=1.0376$.

26d: $C_{16}H_{24}O_3$ (264.36) (structure estimated by MS) methyl ester 25a-d+11a-d: $n_D^{20°}=1.4990$, $d_4^{20°}=1.0462$. 25d: $C_{15}H_{22}O_3$ (250.34) (structure estimated by MS)

EXAMPLE 12

Preparation of formadehydeacetals 30a-d (+11a-d)

67.5 g of the product mixture of Example 3 and 187.5 g formaldehyde-diethylacetal were stirred 4 hours with 3 g KSFcatalyst. Afterwards ethyl alcohol and excess formaldehydediethylacetal were distilled off over a 50 cm glass-bead column. Distillation of the end-product gave 65 g of the formaldhydeethyl acetals 30a-d (+11a-d); $n_D^{20°}=1.5043$; $d_4^{20°}=1.0181$.

30d: $C_{16}H_{26}O_2$ (250.38, estimated by MS).

EXAMPLE 13

Preparation of the dimethoxy-ethyl-derivatives 28a-d (+11a-d) and the oxoacetaldehydes 17a-d (+11a-d)

77 g of the product mixture of Example 3 were mixed with 24 g NaOH (solid) and 4 g Aliquat 336 and added at 140° C. to 49 g (0.4 mol) chloracetaldehyde-dimethylacetal. After 36 hours stirring at boiling temperature it was worked up.

dimethylacetals 28a-d (+11a-d): $n_D^{20°}=1.5015$, $d_4^{20°}=1.0139$. 28d: $C_{17}H_{28}O_3$ (280.41).

56 g of the product mixture of Example 13 were mixed with 200 g of 70% acetic acid and stirred together at 95° C. for 1 hour. Subsequently it was diluted with water, extracted with benzine and worked up as usual.

oxoacetaldehydes 27a-d (+11a-d): $C_{15}H_{22}O_2$ (234.34).

EXAMPLE 14

| Perfume oil with wood character | |
|---|---|
| ylanate (p-tert.butylcyclohexylacetate) | 200 g |
| cedarwood oil, Florida | 120 g |
| galbanum, resinoid | 50 g |

-continued

| Perfume oil with wood character | |
|---|---|
| Mahagonat ® | 70 g |
| coumarin | 10 g |
| oil of patchouli | 30 g |
| linalol | 20 g |
| isobornylacetate | 20 g |
| linalylacetate | 50 g |
| labdanum, resinoid | 20 g |
| Brahmanol ® | 50 g |
| styrollylacetate | 20 g |
| cyclogalbanate, 1 in dipropyleneglycol | 10 g |
| citronella oil | 20 g |
| lactoscatone, 10% in dipropyleneglycol | 5 g |
| | 700 g |

This base mixture possesses a pronounced woody smell with aspects of Fougère. By addition of just 300 g of the new compounds new, original smell aspects are shown, that is addition of

| | | Smell characteristic |
|---|---|---|
| (a) | 11a–d + 12a–d | appreciably woody |
| (b) | 10a–d + 11a–d | fresh, woody-spicy |
| (c) | 13a–d + 11a–d | (absorbing sclaree note) |
| (d) | 22a–d + 11a–d | woody, concrete herby-spicy note fresh, woody, Ambra-apect |

EXAMPLE 15

| Perfume oil with heavy-flowery character | |
|---|---|
| Compounds 10a–d + 11a–d (according to Example 4) | 300 g |
| phenylethylalcohol | 200 g |
| heptylacetate | 70 g |
| ylanate (p-tert. butylcyclohexylacetate) | 80 g |
| oil of citronella | 30 g |
| benzylsalicylate | 40 g |
| dimethylbenzylcarbinylacetate | 120 g |
| di-isobutylcarbinol | 30 g |
| eugenol | 10 g |
| geranylnitrile | 60 g |
| tridecene-2-nitrile, 1% in DPG | 10 g |
| Brahmanol ® | 40 g |
| | 1000 g |

This perfume oil with a relatively high content of the new compounds 10a–d+11a–d shows a long-clinging heavy-flowery, but also fresh note and is therefore especially suitable for perfuming washing agents.

EXAMPLE 16

| Flowery composition | |
|---|---|
| compounds 15a–d + 11a–d (according to Example 6) | 300 g |
| phenylethylalcohol | 100 g |
| geranium oil | 130 g |
| oil of citronella | 130 g |
| phenylacetic acid, 10% in DPG | 10 g |
| α-ionone | 30 g |
| oil of linaloa | 60 g |
| geranylacetate | 10 G |
| phenylethylbutyrate | 5 g |
| cyclamenaldehyde | 25 g |
| phenylacetaldehyde, 50% in DMP | 20 g |
| Brahmanol ® | 50 g |
| diheptylacetate | 30 g |
| indole, 10% in DPG | 10 g |
| greenylisobutyrate | 50 g |
| copper oxide, inactive, 10% in DPG | 20 g |
| isodamascone | 20 g |

| Flowery composition | |
|---|---|
| | 1000 g |

This perfume oil with a high content of new compounds 15a–d+11a–d possesses a radiant flowery smell with aspects of roses, violets and spring flowers.

EXAMPLE 17

| Perfume-base with wood-tobacco-Ambra-smell | |
|---|---|
| ethylethers 22a–d (+11a–d) | 690 g |
| ambroxane, 10% in DPG | 9 g |
| lactoscatone, 10% in DPG | 30 g |
| Timberol ® | 50 g |
| Ambron ® | 30 g |
| indolal, 10% in DPG | 10 g |
| oil of patchouli | 20 g |
| Mahagonat ® | 55 g |
| oxoisophorone | 5 g |
| fantesal, 1% in DPG | 1 g |
| | 900 g |

This base with a large content of the new compounds 22a–d (+11a–d) possesses a novel and harmonic smell-complex with woody, spicy (tobacco) and ambra-like aspects.

We claim:

1. A mixture of compounds of the formula:

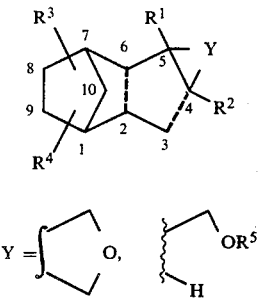

wherein $R^1$ and $R^2$ are a methyl group or a hydrogen atom, one of the substituents being a methyl group and the other a hydrogen atom, $R^3$ and $R^4$ are a methyl group or a hydrogen atom, one of the substituents being a methyl group and the other a hydrogen atom, Y is a tetrahydrofurane system at C-4/C-5 or a substituted oxymethyl group at C-5 and a hydrogen atom at C-4, $R^5$ is a hydrogen atom or $C_1$-$C_6$-acyl-, $C_1$-$C_6$alkyl, $C_1$-$C_6$-alkenyl-, $C_1$-$C_4$ alkoxymethyl, $C_1$-$C_2$ alkoxycarbonyl-, formylmethyl-, or di-$C_1$-$C_4$ alkoxyethyl group and the broken lines indicate a C—C-single bond and a C—C-double bond and or two C—C-single bonds.

2. A process for the preparation of mixtures of dimethyl-tricyclo-[5.2.1.0$^{2,6}$]decane-derivatives, as defined in claim 1, characterized in that dimeric cyclopentadiene is selectively hydrogenated in the norbornane part using transition metal catalysts in normal solvents at a hydrogen pressure of 30–70 bar and a temperature of 20°–80° C.

3. Process according to claim 1, characterized in that the reaction of the partially hydrogenated dimeric methylcyclopentadine is carried out with paraformaldehyde in acetic acid/acetic anhydride using strong acids, at elevated temperature.

4. Process according to claim 1, characterized in the partially hydrogenated methylcycopentadiene dimer is reacted with a solution prepared at boiling temperature of paraformaldehyde in anhydrous formic acid at an elevated temperature.

5. A perfume composition which contains a mixture of the isomers of claim 1, of perfume mixtures and perfume oils for the perfuming of cosmetic and industrial products.

6. A foodstuff composition which contains a mixture of the isomers of claim 1.

7. A process for the preparation of mixtures of dimethyl-tricyclo-[5.2.1.0$^{2,6}$]decane-derivatives as defined in claim 1, characterized in that the norbornane portion of dimeric methylcyclopentadiene is hydrogenated in the presence of hydrogen and a hydrogenation catalyst and thereafter reacted with a reagent selected from the group consisting of formaldehyde, paraformaldehyde and trioxane in a polar solvent in the presence of a protic acid or a Lewis acid.

8. A process as defined in claim 1 wherein the product is saponified with sodium hydroxide and the ester is obtained by reacting the saponified product with an acid anhydride.

9. A process as defined in claim 1 wherein the product is saponified and esterified to form an ester.

10. A process as defined in claim 1 wherein the product is saponified and etherified.

* * * * *